United States Patent [19]

Ruff

[11] Patent Number: 5,342,376

[45] Date of Patent: Aug. 30, 1994

[54] INSERTING DEVICE FOR A BARBED TISSUE CONNECTOR

[75] Inventor: Gregory L. Ruff, Durham, N.C.

[73] Assignee: Dermagraphics, Inc., Durham, N.C.

[21] Appl. No.: 55,870

[22] Filed: May 3, 1993

[51] Int. Cl.$^5$ .............................................. A61B 17/00
[52] U.S. Cl. ....................... 606/151; 606/148; 606/228; 606/230; 606/215
[58] Field of Search ............... 606/187, 155, 215, 154, 606/148, 151, 228, 230

[56] References Cited

U.S. PATENT DOCUMENTS

| | | | |
|---|---|---|---|
| 709,392 | 9/1902 | Brown | 606/221 |
| 733,723 | 7/1903 | Lukens | 606/221 |
| 789,401 | 5/1905 | Acheson | 606/221 |
| 816,026 | 3/1906 | Meier | 606/221 |
| 1,142,510 | 6/1915 | Engle | 606/221 |
| 1,321,011 | 11/1919 | Cottes | 606/221 |
| 1,728,316 | 9/1929 | Von Wachenfeldt | 606/221 |
| 2,201,610 | 5/1940 | Dawson, Jr. | 606/221 |
| 2,232,142 | 2/1941 | Schumann | 606/221 |
| 2,254,620 | 9/1941 | Miller | 606/221 |
| 2,421,193 | 5/1947 | Gardner | 606/215 |
| 2,472,009 | 5/1949 | Gardner | 606/221 |
| 2,684,070 | 7/1954 | Kelsey | 606/221 |
| 2,817,339 | 12/1957 | Sullivan | 606/221 |
| 2,910,067 | 10/1959 | White | 606/221 |
| 3,068,869 | 12/1962 | Sheldon et al. | 606/221 |
| 3,068,870 | 12/1962 | Levin | 606/221 |
| 3,166,072 | 1/1965 | Sullivan, Jr. | 606/221 |
| 3,209,754 | 10/1965 | Brown | 606/221 |
| 3,214,810 | 11/1965 | Mathison | 606/221 |
| 3,221,746 | 12/1965 | Noble | 606/155 |
| 3,234,636 | 2/1966 | Brown | 606/221 |
| 3,273,562 | 9/1966 | Brown | 606/221 |
| 3,378,010 | 4/1968 | Codling et al. | 606/221 |
| 3,385,299 | 5/1968 | LeRoy | 606/221 |
| 3,525,340 | 8/1970 | Gilbert | 606/221 |
| 3,586,002 | 6/1971 | Wood | 606/221 |
| 3,608,095 | 9/1971 | Barry | 606/187 |
| 3,608,539 | 9/1971 | Miller | 606/187 |
| 3,716,058 | 2/1973 | Tanner, Jr. | 606/221 |
| 3,825,010 | 7/1974 | McDonald | 606/216 |
| 4,073,298 | 2/1978 | LeRoy | 606/216 |
| 4,259,959 | 4/1981 | Walker | |
| 4,317,451 | 3/1982 | Cerwin et al. | 606/220 |
| 4,428,376 | 1/1984 | Mericle | 606/220 |
| 4,430,998 | 2/1984 | Harvey et al. | |
| 4,434,796 | 3/1984 | Karapetian et al. | 606/220 |
| 4,454,875 | 6/1984 | Pratt et al. | 606/219 |
| 4,467,805 | 8/1984 | Fukuda | 606/221 |
| 4,505,274 | 3/1985 | Speelman | |
| 4,531,522 | 7/1985 | Bedi et al. | |
| 4,548,202 | 10/1985 | Duncan | |
| 4,610,251 | 9/1986 | Kumar | |
| 4,635,637 | 1/1987 | Schreiber | |
| 4,637,380 | 1/1987 | Orejola | |
| 4,676,245 | 6/1987 | Fukuda | |
| 4,719,917 | 1/1988 | Barrows et al. | |
| 4,841,960 | 6/1989 | Garner | |
| 4,887,601 | 12/1989 | Richards | 606/219 |
| 4,994,073 | 2/1991 | Green | 606/220 |
| 4,997,439 | 3/1991 | Chen | 606/216 |
| 5,002,562 | 3/1991 | Oberlander | 606/221 |
| 5,007,921 | 4/1991 | Brown | 606/221 |
| 5,026,390 | 6/1991 | Brown | 606/221 |
| 5,047,047 | 9/1991 | Yoon | 606/216 |
| 5,192,302 | 3/1993 | Kensey et al. | 606/215 |

Primary Examiner—Stephen C. Pellegrino
Assistant Examiner—Gary Jackson
Attorney, Agent, or Firm—Richard W. Evans

[57] ABSTRACT

An inserting device is disclosed for positioning a barbed tissue connector in tissue to close a wound. The barbed tissue connector is of a type which includes a generally rigid elongated body having a pointed leading end and a plurality of axially spaced barbs on the elongated body. The inserting device comprises a tubular body which is adapted to receive the connector therein with the pointed leading end of the connector protruding from an open leading end of the tubular body. The inserting device and the connector contained therein are positioned in tissue such that at least one of the barbs on the connector is engaging tissue, and the device is then retracted from the tissue, leaving the connector in place.

18 Claims, 3 Drawing Sheets

INSERTING DEVICE FOR A BARBED TISSUE CONNECTOR

CROSS REFERENCE TO RELATED APPLICATION

Reference is made to U.S. Pat. application Ser. No. 08/055,989, now pending, entitled Barbed Tissue Connector, filed in the name of Gregory L. Ruff, on even date herewith.

BACKGROUND OF INVENTION

1. Field of the Invention

This invention relates to an inserting device for a barbed tissue connector, and more particularly, to such a device which can be used to quickly and effectively insert a number of connectors across a body wound.

2. Description of the Prior Art

Human wounds are typically repaired with a filament introduced into the tissue by a needle attached to one end. After piercing the opposing faces of the wound, the needle is removed, and the ends of the suture are tied together with at least three overhand knots. Such a technique requires considerable time and expertise on the part of the surgeon. There are also a number of other drawbacks to repairing a wound in this manner. For example, it is very difficult to use sutures to repair wounds where there is insufficient space to properly manipulate the suture, especially those wounds repaired using fiber optic visualization. The suture forms a loop as it is tied, and this loop constricts blood flow to the tissue in its confines, promoting necrosis of the wound margins. Further, if the needle's passage was noncircular, the tissue will be distorted as it is secured by the suture.

Alternatives to conventional sutures are known in the prior art. Staples, as shown, for example, in U.S. Pat. No. 4,994,073, to Green, are often used for approximating the superficial layer of the wound. Staples, however, are generally unsuitable for deeper layers of tissue.

The patent to Alcamo, U.S. Pat. No. 3,123,077, discloses a roughened suture which can be passed through tissue in one direction, but resists movement in the opposite direction. The Alcamo suture, however, still must be sewn, as by a conventional technique, and the trailing end must be secured with knots. Thus, although there is less slippage of the suture in the wound, most of the disadvantages of sutures noted above are also found in the Alcamo suture.

The patent to Tanner, U.S. Pat. No. 3,716,058, discloses a relatively rigid suture with one or more barbs on opposite ends of an arcuate body. The suture is inserted by means of a notched and slotted needle. One disadvantage of the Tanner suture is that the rigid barbs, which protrude from the needle as the suture is inserted, will lacerate tissue and prevent retrograde repositioning. Further, since the barbs are only located at the ends of the suture, the forces applied to the tissue by the barbs will be limited to a relatively small area; this substantially increases the pressure on the blood vessels ensnared by a barb and severely restricts blood flow to the area.

It will be seen from the foregoing that there is a need for a tissue connector which can be placed more expeditiously than sutures, is self-retaining, obviates distortion of the tissue, can close tissue inaccessible to conventional procedures and which preserves blood flow by broadly distributing the retention force.

SUMMARY OF THE INVENTION

It is an object of the present invention to overcome the problems of known inserting devices for sutures and to provide an improved inserting device for use with a barbed tissue connector.

In accordance with the present invention there is provided an inserting device for use with a barbed tissue connector, the connector comprising an elongated body and a plurality of axially spaced barbs projecting from the elongated body, the barbs being configured such that they are yieldable in the direction of the elongated body and are generally rigid in the opposite direction, the device comprising: a tubular body having an interior of a size sufficient to receive a barbed tissue connector, the tubular body having a leading end having an opening therein and a trailing end having an opening therein, and the opening in the leading end being sufficiently large to permit the connector to be extracted therefrom.

In one embodiment of the present invention, the inserting device comprises a tubular body which is adapted to receive a barbed tissue connector therein with a pointed end of the connector protruding from an open leading end of the tubular body. The inserting device and the connector contained therein are positioned in tissue such that at least one of the barbs on the connector is engaging tissue, and the device is then retracted from the tissue, leaving the connector in place.

The use of the inserting device of the present invention along with a barbed tissue connector permits a surgeon to rapidly and securely attach the edges of a wound in human tissue without the necessity of threading and tying numerous individual stitches or the use of a complicated or elaborate tool. The connector is bioabsorbable so that it does not require a painful and difficult removal by the surgeon after a wound is healed. The inserting device is configured to minimize distortion to tissue when inserted, is capable of insertion into the faces of a wound, can be used to connect tissue at the bottom of a deep wound, and can be used to connect tissue which is inaccessible to a staple. Finally, the inserting device can be used to quickly and accurately insert a connector when the surgeon only has access to tissue from a small opening or from only one direction, as, for example, during an endoscopic procedure.

Other features and advantages will become apparent upon reference to the following description of the preferred embodiment when read in light of the attached drawings.

DESCRIPTION OF THE PREFERRED EMBODIMENTS

The present invention allows a surgeon to rapidly and securely attach the edges of a wound in human tissue without the necessity for threading and tying numerous individual stitches or for using a complicated or elaborate tool. As used herein, the term "wound" means an incision, laceration, cut, or other condition where suturing, stapling, or the use of another tissue connecting device might be required.

Figure 1:
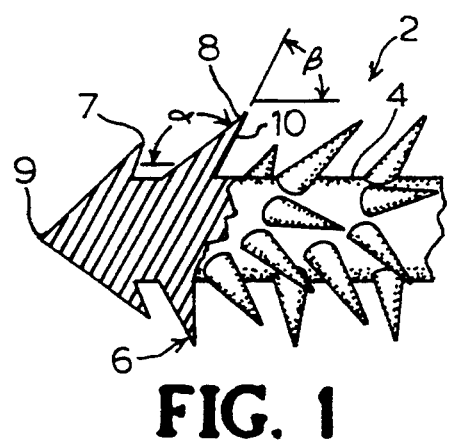
FIG. 1 is a side view of one embodiment of a barbed tissue connector for use with the present invention, with a section of the connector broken away to show an end of the connector.
Figure 2:
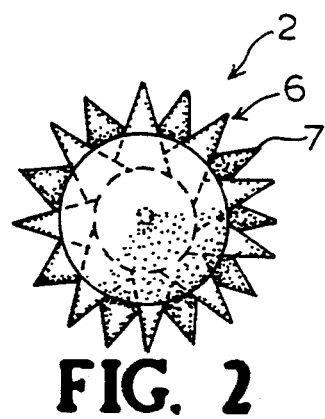
FIG. 2 is an end view of the connector shown in FIG. 1.

With reference to FIGS. 1 and 2, there is shown a barbed tissue connector 2 for use with the present invention. Connector 2 includes a body 4 which is generally circular in cross section and a plurality of closely-spaced barbs 6 which extend around the periphery of the body 4. A pointed end 9 is formed on the body 4 to facilitate penetration of the connector 2 into tissue. The body 4 preferably has sufficient dimensional stability to assume a substantially rigid configuration during use and is sufficiently resilient to return to a predetermined shape after deflection therefrom. In some applications, it may be desirable for the body 4 to be flexible and substantially nonresilient so that the shape of an inserted connector will be determined by surrounding tissue.

Barbs 6 serve to hold the connector in tissue and resist retraction of the connector from the tissue. The barbs 6 can be arranged in any suitable pattern, for example, in a helical pattern as shown in FIG. 1. In a helical pattern of barbs 6, it is preferable that the number of barbs occupying one revolution not be an integer, thereby avoiding parallel axial rows of barbs; such an arrangement provides a more uniform distribution of forces on the tissue and lessens the tendency of an inserted connector 2 to cut through tissue. If the number of barbs in one revolution is not an integer, the barbs in successive revolutions will be offset, as shown in FIG. 2, and the amount of offset will determine which barbs are in axial alignment. For example, if the barbs in successive revolutions are offset by ½ barb, the barbs in every second revolution will be in axial alignment, and by extension, if the barbs in each successive revolution are offset by 1/x barb, the barbs in every x revolution will be in axial alignment.

As shown in FIG. 1, each barb 6 includes a first side 8 which forms an obtuse angle alpha with the body 4 and a second side 10 which forms an acute angle beta with the body 4. Each barb 6 tapers to a point 7, and the amount of difference between the angle alpha of side 8 and angle beta of side 10 will control the amount of taper in the barb 6. A barb 6 which tapers from a broad base to a narrow tip can be effective in resisting retraction, yet will yield toward the body 4 during insertion to reduce the effort and tissue damage associated with insertion of the connector 2. The barbs 6 can be generally conical, as shown in FIG. 1, or the barbs 6 can be any other shape which will function in substantially the same manner as the conical barbs 6.

The configuration of barbs 6 and the surface area of the barbs can vary depending upon the tissue in which the connector 2 is used. The proportions of the barbs 6 can remain relatively constant while the overall length of the barbs and the spacing of the barbs are determined by the tissue being connected. For example, if the connector 2 is intended to be used to connect the edges of a wound in skin or tendon, each barb 6 can be made relatively short to facilitate entry into this rather firm tissue. If the connector 2 is intended for use in fatty tissue, which is relatively soft, the barbs can be made longer and spaced farther apart to increase the holding ability in the soft tissue.

As shown in FIG. 1, the barbs 6 on connector 2 have a uniform unidirectional configuration, that is, the barbs 6 are uniformly spaced on body 4 and all the sides 8 are oriented in the same direction, facing pointed end 9. Connector 2 can be inserted into tissue with the sides 8 of each barb 6 facing in the direction of motion. Connector 2 will prevent movement of tissue in the direction in which it was inserted. A pair of connectors 2 inserted adjacent to each other and in opposite directions will prevent movement of tissue in either direction across a wound.

Connector 2 can be formed of a material sufficiently hard for point 9 to pierce tissue and enable the connector to be inserted in tissue when a substantially axial force is applied to body 4. Connector 2 is preferably composed of a bioabsorbable compound, such as a polyglycolic acid or polylactic acid polymer or copolymer. The use of a bioabsorbable material eliminates the necessity of removing the connector from the patient, which can be a painful and possibly dangerous process. Connector 2 can be formed, for example, by injection molding.

In one representative example of connector 2 for use in muscular tissue, the body 4 is formed from polyglycolic acid, has a length of 1 to 5 cm, and a diameter of about 1 mm. The diameter of a circle extending around points 7 of barbs 6 will be about 3 mm, and the barbs are spaced apart from each other on body 4 by a distance of 1 mm. Side 8 forms an angle of 135 degrees with the body 4 and side 10 forms an angle of 75 degrees with the body 4.

Figure 3:
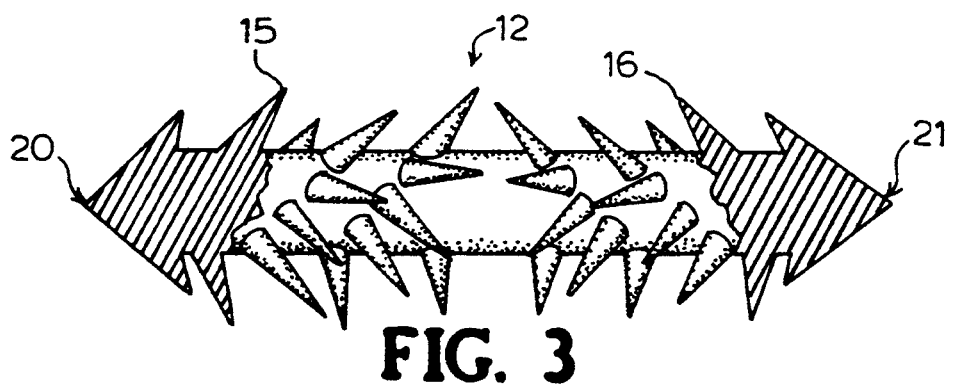
FIG. 3 is a side view of another embodiment of a connector for use with the present invention, with sections of the connector broken away to show the ends of the connector.

In FIG. 3, there is shown a second embodiment of the present invention in which barbs 16 are arranged in a uniform bidirectional configuration on a barbed tissue connector 12. Barbs 16 are constructed in the same manner as barbs 6 on connector 2. A first set of barbs 15 on connector 12 are arranged in a helical pattern and face a pointed end 20, and a second set of barbs 16 on connector 12 are arranged in a helical pattern and face a pointed end 21. Each of the pointed ends 20, 21 should be sufficiently hard and sharp to easily penetrate tissue in which the connector is to be used. Connector 12 is particularly suitable for applications where the edges of a wound are prone to separate. Connector 12 can be used by inserting one of the ends, for example end 20, into a first side of a wound (not shown), spreading the wound slightly to expose the second side of the wound, inserting the end 21 of the connector 12 into the second side of the wound, and then pressing the edges of the wound together. The barbs 15 and 16 on the ends of the connector 12 will grasp the tissue on each side of the wound and prevent the edges of the wound from spreading.

Figure 4:
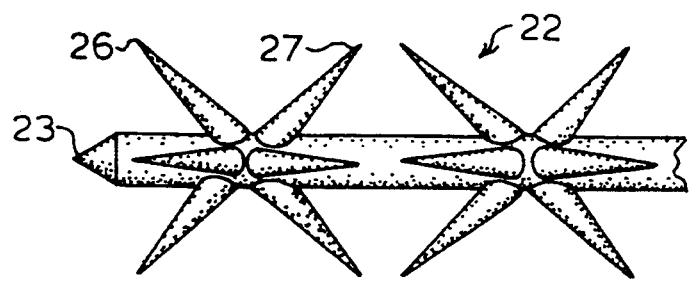
FIG. 4 is a side view of another embodiment of a connector for use with the present invention.

With reference to FIG. 4, there is shown another embodiment of the present invention in which a barbed tissue connector 22 has a nonuniform bidirectional configuration. Connector 22 comprises a pointed end 23 and one or more barbs 26 facing a first direction which alternate with one or more barbs 27 facing a second direction. At each axial location, there can be a number, e.g. 4-9, of circumferentially-spaced barbs 26 or 27. To insert connector 22 into tissue, the surgeon would use an inserting device 80 as described below. The barbs 26 and 27 on connector 22 are arranged to prevent any localized movement of tissue relative to the connector in an axial direction.

Figure 5:
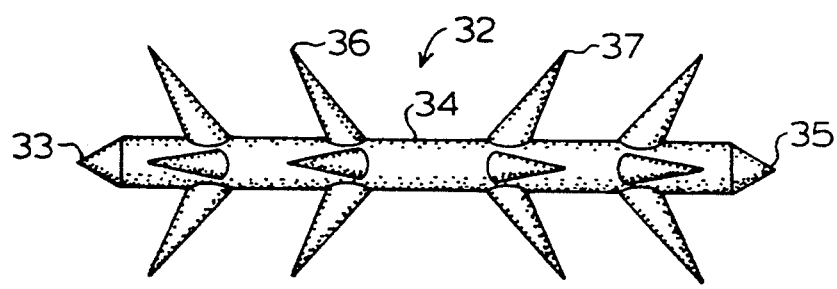
FIG. 5 is a side view of another embodiment of a connector for use with the present invention.

With reference to FIG. 5, there is shown another embodiment of the present invention in which a barbed tissue connector 32 has a uniform bidirectional configuration. Connector 32 comprises a body 34 having pointed ends 33 and 35. A plurality of axially-spaced barbs 36 adjacent pointed end 33 face toward end 35, and a plurality of axially-spaced barbs 37 adjacent pointed end 35 face toward end 33. Barbs 36 and 37 can be circumferentially-spaced around body 34 at each axial location, or the barbs 36 and 37 can be of the same construction and arranged in the same pattern as barbs 6 on connector 2. To insert a connector 32, the surgeon would use an inserting device 80 as described below. If the body 34 of the connector 32 is sufficiently rigid, the connector 32 would prevent tissue retained by the barbs 36 from moving toward end 35 and tissue retained by barbs 37 from moving toward end 33. It will be apparent that only one end of connector 32 needs to be pointed; two pointed ends are preferable, however, so that the surgeon does not have to take the time to insure that connector 32 is oriented in the inserting device 80 with a pointed end protruding from the inserting device.

Figure 6:
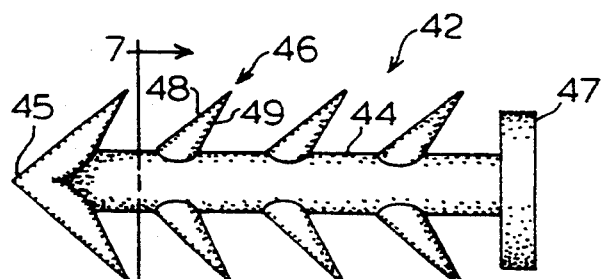
FIG. 6 is a side view of another embodiment of a connector for use with the present invention.
Figure 7:
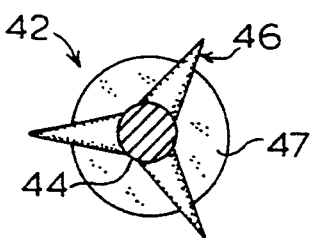
FIG. 7 is a sectional view taken along the line 7—7 in FIG. 6.

With reference to FIGS. 6 and 7, there is shown another embodiment of the present invention in which a barbed tissue connector 42 comprises a body 44 having a pointed end 45 for penetration into tissue. A head 47 is formed on an opposite end of body 44. A plurality of circumferentially-spaced barbs 46 are formed on body 44 at each of a number of axial locations. As shown in FIG. 7, three barbs 46 are formed at each axial location; however, more or less than three barbs 46 could be used for certain applications. Barbs 46 include a first side 48 formed at an obtuse angle to the body 44 and a second side 49 which projects from body 44 at an acute angle. The connector 42 can be forced into tissue by applying a force to the head 47. The connector 42 can be applied by hand, or it can be inserted using an inserting device 80 as described below.

The connector 42 can be formed entirely of a bioabsorbable material, or the head 47 and the body 44 can be composed of different materials. For example, the body 44 can be composed of a bioabsorbable material, and the head 47 can be composed of metal for superior strength and to facilitate insertion of the connector 42. Head 47 can be made flat, as shown in FIG. 6, or the head can be formed by a single ring of barbs (not shown) facing in a direction opposite to that of the barbs 46.

In use, a series of connectors 42 can be inserted into tissue, such as along the edges and in the field of a skin graft. After an adequate amount of time has passed for the wound to heal, the tissue beneath each head 47 could be depressed slightly to permit the head 47 to be cut from the body 44. The tissue would then rise up over the cut end of the body. Such a process would reduce scarring which could result from a long-term projection of the body 44 through tissue and would eliminate the necessity to remove connectors 42 from the patient.

Figure 8:
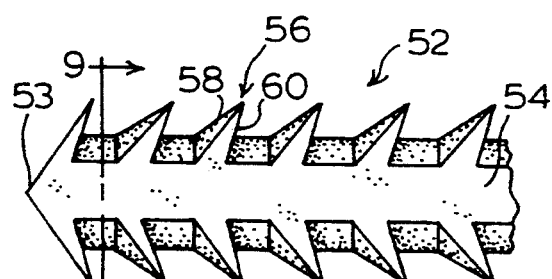
FIG. 8 is a side view of another embodiment of a connector for use with the present invention.
Figure 9:
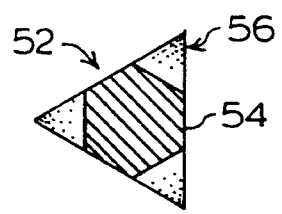
FIG. 9 is a sectional view taken along the line 9—9 in FIG. 8.

With reference to FIGS. 8 and 9, there is shown another embodiment of the present invention in which a barbed tissue connector 52 has a uniform unidirectional configuration. Connector 52 comprises a body 54 having a non-circular cross-sectional shape. Body 54 includes a plurality of barbs 56 which are generally triangular in cross section and are equally spaced around the periphery of the body at a series of axial locations. Each of the barbs 56 includes a first side 58 disposed at an obtuse angle to body 54 and a second side 60 disposed at an acute angle to the body. Body 54 includes a pointed end 53 to facilitate entry in tissue. Use of a non-circular cross-sectional shape increases the surface area of the connector 52 and facilitates the formation of the multiple barbs on the connector. For example, barbs 56 can be formed on a piece of stock having a triangular cross section by removing material at successive axial locations from the three edges of the stock. It will be apparent that a similar process could be used to form barbs on stock of a different cross section (not shown), for example, a rectangular or hexagonal cross section.

Figure 10:
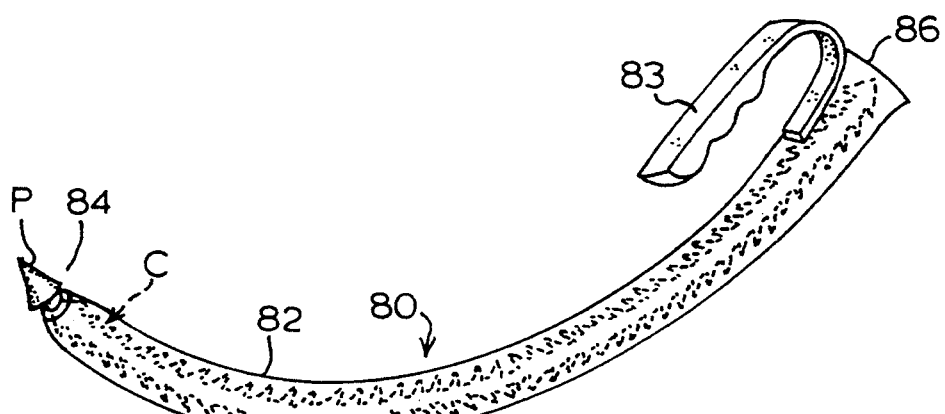
FIG. 10 is a perspective view of the inserting device of the present invention.
Figure 11:
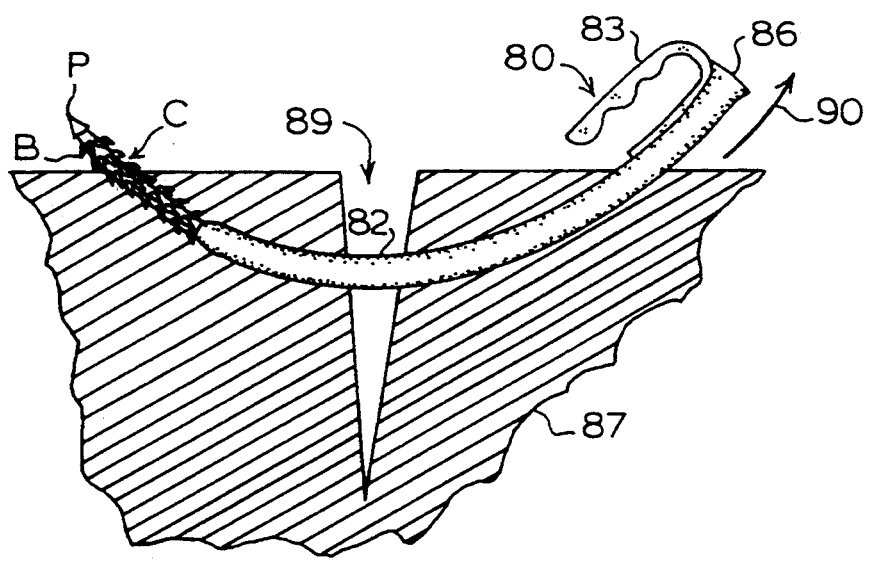
FIG. 11 is a view showing the inserting device and connector in a wound.

In the use of the disclosed connectors, such as connectors 2 and 42, the surgeon can grip the connector in one hand and push the connector into the tissue. As an alternative to directly inserting the connectors into the tissue, the surgeon can use an inserting device 80 as shown in FIGS. 10 and 11. The inserting device 80 comprises a circular tubular body 82. The tubular body 82 can be generally arcuate in an axial direction, and the body 82 is sufficiently long to contain at least a portion of a barbed tissue connector C. Device 80 has an inwardly tapered leading end 84 and an outwardly tapered, or flared, trailing end 86. A handle 83 is provided on body 82 adjacent trailing end 86 to enable the surgeon to manipulate the inserting device 80.

In order to facilitate entry of the connector C and the device 80 into tissue, a connector C is positioned in tubular body 82 with a pointed end P of the connector C extending from leading end 84. In a preferred embodiment, the interior diameter of the body 82 is made slightly smaller than the outside diameter of the connector C so that the barbs B of a connector C in the body 82 will press against the body 82; as a result, the connector C will be retained in the body 82 during insertion in tissue with the point P properly positioned outside of the body 82. The connector can also be positioned in body 82 with a barb B outside of body 82 to insure that the connector C will not be pushed back in the body 82 during insertion. In one application of device 80, the surgeon inserts the body 82 having connector C therein into the patient's tissue 87 until the connector C reaches a desired position, for example, the position shown in FIG. 11. Device 80 is then withdrawn in the direction of arrow 90, and a barb, or barbs, B on the connector C penetrates and catches the tissue 87 to hold the connector C in the inserted position.

Use of the inserting device 80 is particularly recommended when the connector C includes multiple barbs facing more than one direction, such as connectors 22 and 32, or when the connector is too flexible for insertion without additional support.

While the present invention has been described with respect to certain preferred embodiments thereof, it is to be understood that numerous variations in the details of construction, the arrangement and combination of parts, and the type of materials used may be made without departing from the spirit and scope of the invention.

What is claimed is:

1. A device for insertion into tissue, comprising:
   a barbed tissue connector having an elongated body and a plurality of axially spaced barbs projecting from said elongated body, and extending along a substantial portion of the length of said elongated body said barbs being configured such that they are yieldable in the direction of said elongated body and are generally rigid in the opposite direction; and
   a tubular body having an interior of a size sufficient to receive the barbed tissue connector, said tubular body having a leading end having an opening therein and a trailing end having an opening therein, and said opening in said leading end being sufficiently large to permit said connector to be extracted therefrom.

2. A inserting device, as recited in claim 1, wherein said tubular body is substantially rigid.

3. An inserting device, as recited in claim 1, wherein said leading end is tapered inwardly to facilitate the insertion of said device in tissue.

4. An inserting device, as recited in claim 1, wherein said trailing end is tapered outwardly to facilitate the insertion of said connector in said tubular body.

5. An inserting device, as recited in claim 1, wherein said tubular body has a generally circular cross section.

6. An inserting device, as recited in claim 5, wherein an inside diameter of said tubular body is slightly less than an outside diameter of said connector.

7. An inserting device, as recited in claim 1, wherein said tubular body is generally arcuate in an axial direction.

8. An inserting device, as recited in claim 1, wherein said device has a handle on said tubular body adjacent said trailing end.

9. An inserting device, as recited in claim 1, wherein at least one barb of said connector protrudes from said opening in the leading end of the tubular body.

10. An inserting device, as recited in claim 1, wherein the body of said connector has a leading end which is of a shape to facilitate penetration into said tissue.

11. A inserting device, as recited in claim 11, wherein the shape of the leading end of said connector forms a point.

12. An inserting device, as recited in claim 12, wherein the body of said connector is formed of a material sufficiently hard for said point to pierce tissue and enable said connector to be inserted in tissue when a substantially axial force is applied to said body.

13. An inserting device, as recited in claim 1, wherein the interior diameter of said tubular body is slightly smaller that the outside diameter of said connector so that the barbs of the connector in the tubular body will yieldably press against the interior of the body to facilitate the retention of the connector in the tubular body while being inserted into tissue.

14. A method of connecting tissue using a barbed tissue connector having an elongated body and a plurality of axially spaced barbs projecting from said elongated body, said elongated body having a pointed end, said barbs being configured such that they are yieldable in the direction of said elongated body and are generally rigid in the opposite direction, said method comprising the steps of:
   positioning said connector in an inserting device having a tubular body such that said pointed end and at least one barb protrude from said tubular body;
   inserting the device having the connector therein into tissue such that said one barb is engaging tissue; and
   moving said device relative to said connector to extract the device from the tissue while leaving the connector in the tissue.

15. A method, as defined in claim 14, wherein said connector includes a first set of barbs facing said pointed end and a second set of barbs facing an opposite end of said connector.

16. A device for use in repairing a wound, said device comprising:
   a tubular body having a leading end with an opening therein and a trailing end with an opening therein; and
   a barbed tissue connector having an elongated body and a pointed end on said elongated body, said connector having a plurality of axially spaced barbs projecting from said elongated body, and said connector being positioned in said tubular body with said pointed end protruding from said opening in the leading end.

17. A device, as recited in claim 16, wherein at least one barb protrudes from said opening in the leading end.

18. A device, as recited in claim 17, wherein said tubular body is generally arcuate in an axial direction.

* * * * *

UNITED STATES PATENT AND TRADEMARK OFFICE
CERTIFICATE OF CORRECTION

PATENT NO. : 5,342,376
DATED : August 30, 1994
INVENTOR(S) : Dr. Gregory L. Ruff It is certified that error appears in the above-identified patent and that said Letters Patent is hereby corrected as shown below:

Column 7,
Line 26, change "A" to -- An --.

Column 8,
Line 1, change "A" to -- An --.
Line 1, change "claim 11" to -- claim 10 --.

Signed and Sealed this

Second Day of May, 2006

JON W. DUDAS
*Director of the United States Patent and Trademark Office*